United States Patent

Hajek et al.

[11] 4,002,601
[45] Jan. 11, 1977

[54] URETHANE OXAZOLIDINES

[75] Inventors: Manfred Hajek, Cologne; Kuno Wagner, Leverkusen, both of Germany

[73] Assignee: Bayer Aktiengesellschaft, Leverkusen, Germany

[22] Filed: Sept. 18, 1975

[21] Appl. No.: 614,470

[30] Foreign Application Priority Data

Sept. 28, 1974 Germany .................. 2446438

[52] U.S. Cl. .................. 260/77.5 AT; 260/244 R; 260/307 FA; 260/333
[51] Int. Cl.$^2$ ................ C08G 18/06; C07D 265/04
[58] Field of Search ............... 260/77.5 AT, 244 R, 260/333, 307 FA

[56] References Cited

UNITED STATES PATENTS

| | | | |
|---|---|---|---|
| 3,661,923 | 5/1972 | Emmons et al. | 260/244 R X |
| 3,743,626 | 7/1973 | Emmons | 260/77.5 AQ |
| 3,859,299 | 1/1975 | Hocker et al. | 260/244 R X |
| 3,864,335 | 2/1975 | Emmons | 260/240 R |

*Primary Examiner*—Lewis T. Jacobs
*Attorney, Agent, or Firm*—Gene Harsh; Lawrence S. Pope; Frederick H. Colen

[57] ABSTRACT

This invention relates to compounds corresponding to the following general formula:

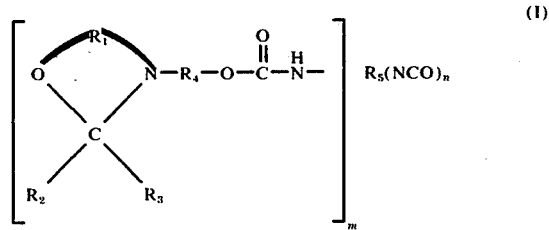

wherein
m represents an integer of from 1 to 6;
n represents an integer of from 0 to 4;
$R_1$ represents an aliphatic hydrocarbon group containing from 2 to 6 carbon atoms;
$R_2$ and $R_3$ which may be the same or different, each represents hydrogen, an aliphatic hydrocarbon group containing from 1 to 4 carbon atoms, a cycloaliphatic hydrocarbon group containing from 5 to 7 carbon atoms, or an aromatic hydrocarbon group containing from 6 to 10 carbon atoms, or when taken together with the ring carbon atom they may form a 5- or 6-membered cycloaliphatic hydrocarbon ring;
$R_4$ represents an aliphatic hydrocarbon group containing from 2 to 6 carbon atoms; and
$R_5$ represents a residue of the type which may be obtained by removing the isocyanate groups from an organic (n + m)-valent polyisocyanate.

The invention also relates to a process for preparing urethanes which contain oxazolidine groups and optionally isocyanate groups, characterized in that N-hydroxyalkyl-oxazolidines are reacted with organic polyisocyanates at an OH/NCO ratio of from 1:1 to 1:6.

6 Claims, No Drawings

URETHANE OXAZOLIDINES

BACKGROUND OF THE INVENTION

Compounds which contain the characteristic group:

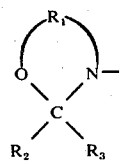
(II)

and which will hereinafter be referred to as "oxazolidines" for the sake of simplicity, have the interesting property that by the action of water (moisture) they may be converted hydrolytically into derivatives which contain hydroxyl and secondary amino groups, i.e., $HO-R_1-NH$ groups. These oxazolidines are therefore potential reactants for organic polyisocyanates. Mixtures of such oxazolidines with polyisocyanates are therefore systems which may be hardened by the action of water. According to the teaching of German Offenlegungsschrift No. 2,018,233 and U.S. Pat. No. 3,743,626, this principle is applied to certain polyester oxazolidines which may be prepared in accordance with German Offenlegungsschrift Nos. 1,952,091 and 1,952,092 and U.S. Pat. Nos. 3,661,923 and 3,864,335. The polyester oxazolidines disclosed in the said publications, however, have certain disadvantages with regard both to the process by which they are produced and to the properties of the materials produced from them in accordance with this principle. They are prepared by a transesterification reaction which proceeds slowly even in the presence of catalysts and which must be carried out at temperatures below 160° C. in order to prevent side reactions. The ester groups are found unchanged in the end-products obtained after hydrolytic ring opening followed by the isocyanate polyaddition reaction, so that even the completely hardened end-products of German Offenlegungsschrift No. 2,018,233 have the major disadvantage common to all synthetic resins which contain ester groups of having little resistance to hydrolysis.

SUMMARY OF THE INVENTION

These disadvantages are overcome by the present invention. In the process according to the present invention, the products according to the invention are prepared smoothly by a simple isocyanate addition reaction between N-hydroxyalkyl-oxazolidines and organic polyisocyanates. The finding that no by-products are produced in this reaction which may, if desired, also be carried out in the presence of the conventional catalysts used for the isocyanate polyaddition reaction is surprising since such difficulties would in principle be expected on the grounds that compounds which contain the structural unit $O-CH_2-N<$ are known to have a pronounced tendency to react with isocyanates, resulting in the insertion and removal of groups (R. Oda et al., Bull. Inst. Chem. Research, Kyoto Univ. 34, 224 – 34 (1956), C.A. 51, 6528 d).

If the preferred polyisocyanates which are free from ester groups are used for the process according to the invention, the resulting compounds according to the invention which are free from ester groups are distinguished from the above mentioned prior art compounds by their substantially increased resistance to hydrolysis, in particular in the alkaline range.

The compounds according to the invention may be prepared by reacting N-hydroxyalkyl-1,3-oxazolidines corresponding to the following general formula:

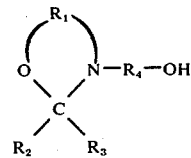
(III)

with polyisocyanates corresponding to the following general formula:

$$R_5(NCO)_{m+n}$$

In these formulae, m, n, $R_1$, $R_2$, $R_3$, $R_4$ and $R_5$ are as defined for formula I. It is preferable to use those N-hydroxyalkyl-oxazolidines of formula III for the process according to the invention wherein $R_1$ represents an aliphatic hydrocarbon group containing 2 or 3 carbon atoms; $R_2$ and $R_3$, which may be the same or different, each represents hydrogen or an aliphatic hydrocarbon group containing from 1 to 4 carbon atoms, and $R_4$ represents an aliphatic hydrocarbon group containing 2 or 3 carbon atoms. These preferred N-hydroxyalkyl-oxazolidines, of course, give rise to the corresponding compounds according to the invention, i.e., compounds of the general formula mentioned above wherein $R_1$, $R_2$, $R_3$, and $R_4$ have the last-mentioned, preferred meanings.

DETAILED DESCRIPTION OF THE INVENTION

The N-hydroxyalkyl-oxazolidines used in the process according to the invention are prepared by methods known in the literature in which a condensation reaction between a ketone or aldehyde and a bis-(hydroxyalkyl)-amine is accompanied by ring closure and dehydration, and the water of reaction is removed azeotropically with an inert carrier or with the carbonyl compound used in excess.

The carbonyl compounds corresponding to the formula:

(V)

wherein $R_2$ and $R_3$ are as defined for formula I are suitable for this reaction. Included are the following aldehydes and ketones: formaldehyde, acetaldehyde, propionaldehyde, butyraldehyde, isobutyraldehyde, benzaldehyde, tetrahydrobenzaldehyde, acetone, methyl ethyl ketone, methyl propyl ketone, methyl isopropyl ketone, diethyl ketone, methyl butyl ketone, methyl isobutyl ketone, methyl-t-butyl ketone, diisobutyl ketone, cyclopentanone and cyclohexanone. In accordance with the definition given above of the preferred identities for the groups $R_2$ and $R_3$, the carbonyl compounds preferably used are formaldehyde and $C_2$ to $C_8$ aliphatic aldehydes and ketones.

Suitable bis-(hydroxyalkyl)-amines corresponding to the formula:

$$HO-R_1-NH-R_4-OH \quad (VI)$$

are, in particular, bis-(2-hydroxyethyl)-amine and bis-(2-hydroxypropyl)-amine. In principle, however, the following compounds, for example, are equally suitable: bis-(2-hydroxybutyl)-amine, bis-(2-hydroxyhexyl)-amine, bis-(3-hydroxyhexyl)-amine and N-(2-hydroxypropyl)-N-(6-hydroxyhexyl)-amine.

The polyisocyanates (IV) used in the process according to the invention are preferably those in which the sum of m+n is 2 or 3, i.e., the diisocyanates and triisocyanates known in polyurethane chemistry. The group $R_5$ in the above formula (IV) may be either a hydrocarbon group, in particular an aliphatic hydrocarbon group containing from 4 to 12 carbon atoms, a cycloaliphatic hydrocarbon group containing from 5 to 15 carbon atoms, an aromatic hydrocarbon group containing from 6 to 15 carbon atoms or an araliphatic hydrocarbon group containing from 7 to 15 carbon atoms, i.e. a group of the type which may be obtained by removing the isocyanate groups from a simple di- or tri-isocyanate which contains only hydrocarbon groups in addition to the isocyanate groups, or $R_5$ may also be a group of the type which may be obtained by removing isocyanate groups from a modified organic polyisocyanate. Such modified polyisocyanates, which are preferably di- or tri-isocyanates, include, e.g., the modified polyisocyanates known in polyurethane chemistry which contain urea, allophanate, biuret, isocyanurate, carbodiimide or urethane groups. Besides the simple polyisocyanates or hydrocarbon polyisocyanates mentioned above, diisocyanates or triisocyanates which contain urethane groups are equally preferred for the process according to the invention, particularly those which may be obtained in a conventional manner by reacting excess quantities of the above-mentioned simple (hydrocarbon) diisocyanates with dihydroxy or trihydroxy polyethers of the type known in polyurethane chemistry, which have molecular weights of from about 400 to 10,000, preferably from about 1,000 to 6,000.

It is, of course, also possible in priniciple to use monoisocyanates for the process according to the invention. In that case, compounds according to the invention are obtained wherein n in the above-mentioned formula represents 0 and m represents 1.

The following are examples of the preferred diisocyanates and triisocyanates: tetramethylene-1,4-diisocyanate, hexamethylene-1,6-diisocyanate, dodecane-1,12-diisocyanate, cyclohexane-1,3- and -1,4-diisocyanate and mixtures of these isomers, 1-isocyanato-3,3,5-trimethyl-5-isocyanatomethylcyclohexane (Auslegeschrift No. 1,202,785), hexahydrotolylene-2,4- and -2,6-diisocyanate and mixtures of these isomers, hexahydrophenylene-1,3- and/or -1,4-diisocyanate, perhydrodiphenylmethane-2,4'-and/or -4,4'-diisocyanate, phenylene-1,3- and -1,4-diisocyanate, tolylene-2,4- and -2,6-diisocyanate and mixtures of these isomers, diphenylmethane-2,4'-and/or -4,4'-diisocyanate, naphthylene-1,5-diisocyanate, p-xylylene diisocyanate and triphenylmethane-4,4',4''-triisocyanate. Polyisocyanates with carbodiimide groups as described in German Patent No. 1,092,007, diisocyanates of the type described in U.S. Pat. No. 3,492,330, polyisocyanates containing allophanate groups as described, e.g. in British Patent No. 994,890, Belgian Patent No. 761,626 and published Dutch Patent Application No. 7,102,524, polyisocyanates which contain isocyanurate groups as described, e.g. in German Patent Nos. 1,022,789; 1,222,067 and 1,027,394 and in German Offenlegungsschrift Nos. 1,929,034 and 2,044,048, polyisocyanates which contain urethane groups as described, e.g. in Belgian Patent No. 752,261 or in U.S. Pat. No. 3,394,164, polyisocyanates which contain acylated urea groups according to German Patent No. 1,230,778, polyisocyanates which contain biuret groups as described, e.g. in German Patent No. 1,101,394, in British Patent No. 889,050 and in French Patent No. 7,017,514, polyisocyanates prepared by telomerization reactions as described, e.g. in Belgian Patent No. 723,640, polyisocyanates containing ester groups, such as those mentioned, e.g. in British Patent Nos. 956,474 and 1,072,956, in U.S. Pat. No. 3,567,763 and in German Patent No. 1,231,688 and reaction products of the above-mentioned isocyanates with acetals in accordance with German Patent No. 1,072,385 are also suitable.

As already indicated, isocyanate prepolymers of the type which may be obtained by methods known in the literature by reacting the above-mentioned diisocyanates with compounds which contain at least two hydrogen atoms capable of reacting with isocyanates and which generally have a molecular weight of from about 400 to 10,000 may also be used for the process according to the invention. Among these isocyanate prepolymers may be included, not only compounds which contain amino groups, thiol groups or carboxyl groups, but preferably, also polyhydroxyl compounds, particularly compounds which contain from 2 to 8 hydroxyl groups and especially those with a molecular weight of from about 400 to 10,000, preferably from about 1,000 to 6,000, e.g. polyesters, polyethers, polythioethers, polyacetals, polycarbonates and polyester amides containing at least 2, generally from 2 to 8 and preferably from 2 to 4 hydroxyl groups, of the type which are known for producing both homogeneous and cellular polyurethanes.

The hydroxyl polyethers which may be used according to the invention and which contain at least 2, generally from 2 to 8 and preferably 2 or 3 hydroxyl groups are known and may be prepared, e.g. by polymerizing epoxides, such as ethylene oxide, propylene oxide, butylene oxide, tetrahydrofuran, styrene oxide or epichlorohydrin, either each on its own, e.g. in the presence of $BF_3$, or by an addition reaction of these epoxides, optionally as mixtures or successively, with starting components which contain reactive hydrogen atoms, such as alcohols or amines, e.g. water, ethylene glycol, propylene-1,3- or -1,2-glycol, trimethylol propane, 4,4'-dihydroxydiphenylpropane, aniline, ammonia, ethanolamine or ethylene diamine. Sucrose polyethers of the type described, e.g. in German Auslegeschrift Nos. 1,176,358 and 1,064,938 may also be used according to the invention. Polyethers which have been modified with vinyl polymers, e.g. the polyethers obtained by polymerizing styrene or acrylonitrile in the presence of polyethers (U.S. Pat. Nos. 3,383,351; 3,304,273; 3,523,093; and 3,110,695 and German Patent No. 1,152,536) are also suitable.

Among the polythioethers may be particularly mentioned the condensation products of thiodiglycol on its own and/or with other glycols, dicarboxylic acids, formaldehyde, aminocarboxylic acids or amino alcohols. The products obtained may be polythio mixed ethers, polythioether esters or polythioether ester amides, depending on the co-components.

Suitable polyacetals include, e.g. the compounds which may be obtained from glycols, such as diethylene glycol, triethylene glycol, 4,4'-dioxethoxy-diphenyl-dimethylmethane, hexanediol and formaldehyde. Polyacetals which are suitable for the invention may also be prepared by the polymerization of cyclic acetals.

Suitable known polycarbonates with hydroxyl groups include those which may be prepared, e.g. by reacting diols, such as propane-1,3-diol, butane-1,4-diol and/or hexane-1,6-diol, diethyleneglycol, triethylene glycol or tetraethylene glycol, with diarylcarbonates, e.g. diphenyl-carbonate or phosgene.

The polyesteramides and polyamides which may be used include, e.g. the predominantly linear condensates obtained from polybasic saturated and unsaturated carboxylic acids or anhydrides, and polyvalent saturated and unsaturated amino alcohols, diamines, polyamines and mixtures thereof.

Polyhydroxyl compounds which already contain urethane or urea groups and modified or unmodified natural polyols, such as castor oil, carbohydrates and starch, may also be used. Addition products of alkylene oxides to phenol/formaldehyde resins or to urea/formaldehyde resins may also be used according to the invention.

For particular purposes in which the stability to alkalies is of no importance, the isocyanate, prepolymers may also be synthesized from polyesters.

Suitable polyesters which contain hydroxyl groups include, e.g. the reaction products of polyhydric, preferably dihydric, alcohols, with the optional addition of trihydric alcohols, and polybasic, preferably dibasic, carboxylic acids. Instead of the free polycarboxylic acids, the corresponding polycarboxylic acid anhydrides or esters of lower alcohols or mixtures thereof may be used for preparing the polyesters. The polycarboxylic acids may be aliphatic, cycloaliphatic, aromatic and/or heterocyclic and may be substituted, e.g. with halogen atoms, and/or be unsaturated. The following are given as examples: succinic acid, adipic acid, suberic acid, azelaic acid, sebacic acid, phthalic acid, isophthalic acid, trimellitic acid, phthalic acid anhydride, tetrahydrophthalic acid anhydride, hexahydrophthalic acid anhydride, tetrachlorophthalic acid anhydride, endomethylenetetrahydrophthalic acid anhydride, glutaric acid anhydride, maleic acid, maleic acid anhydride, fumaric acid, dimeric and trimeric fatty acids, such as oleic acid, optionally mixed with monomeric fatty acids, dimethylterephthalate or bis-glycol terephthalate. Suitable polyhydric alcohols include, e.g. ethylene glycol, propylene-1,2- and -1,3-glycol, butylene-1,4- and -2,3-glycol, hexane-1,6-diol, octane-1,8-diol, neopentylglycol, cyclohexane dimethanol (1,4-bis-hydroxymethylcyclohexane), 2-methyl-propane-1,3-diol, glycerol, trimethylolpropane, hexane-1,2,6-triol, butane-1,2,4-triol, trimethylolethane, pentaerythritol, quinitol, mannitol and sorbitol, methyl glycoside, diethyleneglycol, triethylene glycol, tetraethyleneglycol, polyethyleneglycols, dipropyleneglycol, polypropyleneglycols, dibutylene glycol and polybutyleneglycols. The polyesters may also contain a proportion of carboxyl end groups. Polyesters of lactones, such as -caprolactone, or hydroxycarboxylic acids, such as ω-hydroxycaproic acid, may also be used.

Representatives of these compounds which may be used according to the invention have been described, e.g. in High Polymers, Vol. XVI, "Polyurethanes: Chemistry and Technology" by Saunders-Frisch, Interscience Publishers, New York, London, Volume I, 1962, pages 32–42 and pages 44–54 and Volume II, 1964, pages 5–6 and 198–199 and in Kunststoff-Handbuch, Volume VII, Vieweg-Hochtlen, Carl-Hanser-Verlag, Munich, 1966, e.g. on pages 45 to 71.

The products according to the invention are obtained by chemical addition of N-hydroxyalkyl-1,3-oxazolidines to isocyanates. The stoichiometric proportions of the starting components used for this reaction may vary within wide limits according to the intended use. The stoichiometric ratio between the OH groups of the oxazolidine derivatives and the NCO groups may vary from about 4:1 to 1:20 in the reaction mixture. If proportions of from about 4:1 to 1:1 are used, all the isocyanate groups present undergo reaction and the oxazolidine alcohol which may then be present in excess may either be removed or serve as reactive diluent. If the ratio is less than 1, statistically only part of the NCO groups present undergo reaction. The preferred stoichiometric ratios are from about 1:1 to 1:6 and, in particular, from about 1:1 to 1:3. The numerical values for m and n in the formulae given above of the compounds according to the invention depend, of course, on the selected OH/NCO equivalent ratio while the sum of n+m corresponds to the functionality of the polyisocyanate used. Thus, for example, when 1 mol of monoisocyanate is reacted with 1 mol of hydroxyalkyloxazolidine, the numerical values for m and n in the compounds according to the invention are m = 1 and n = 0. When 1 mol of hydroxyalkyloxazolidine is reacted with 1 mol of triisocyanate, compounds according to the invention in which m = 1 and n = 2 are obtained. When 2 mols of hydroxyalkyloxazolidine are reacted with 1 mol of diisocyanate, compounds according to the invention in which m = 2 and n = 0 are obtained.

The process according to the invention may in principle be carried out by adding the oxazolidine alkanol to the isocyanate component but if the OH/NCO ratio is greater than or equal to 1, the sequence may be reversed. If necessary, the oxazolidine derivative and/or the isocyanate may be diluted with a suitable inert solvent, e.g. in order to adapt the viscosity to the technical requirements of the application of the product. The addition reaction itself is carried out at temperatures of from about 10° to 120° C but preferably at temperatures of from about 15° to 80° C.

The course of the reaction is followed by infra-red spectroscopy. Titration of the NCO value as described, e.g. in Houben-Weyl, Methoden der organischen Chemie, Volume II, 4th Edition, Georg Thieme Verlag Stuttgart 1953, on page 557, is interfered with by the oxazolidine ring.

According to the invention, conventional catalysts are often used, e.g. tertiary amines, such as triethylamine, tributylamine, N-methylmorpholine, N-ethylmorpholine, N-cocomorpholine, N,N,N',N'-tetramethyl-ethylenediamine or 1,4-diazabicyclo-(2,2,2)-octane.

Organometallic compounds may also be used as catalysts according to the invention, particularly organo tin compounds.

The organo tin compounds used are preferably tin (II) salts of carboxylic acids, such as tin(II)acetate, tin(II) octoate, tin(II)ethylhexoate and tin(II)-laurate and the dialkyl tin salts of carboxylic acids, such as dibutyl tin diacetate, dibutyl tin dilaurate, dibutyl tin maleate or dioctyl tin diacetate.

Other representatives of catlaysts which may be used according to the invention and the mode of action of these catalysts have been described in Kunststoff Handbuch, Volume VII, published by Vieweg and Hochtlen, Carl-Hanser Verlag, Munich, 1966, e.g. on pages 96 to 102 and in High Polymers, Vol. XVI, "Polyurethanes: Chemistry and Technology" by Saunders-Frisch, Interscience Publishers, New York, London, Volume I, 1962, pages 129 to 215.

The catalysts are generally used in a quantity of from about 0.001 to 10% by weight, based on the total quantity of reactants.

The catalysts mentioned above have the advantage that they do not interfere with subsequent use of the resulting oxazolidine urethanes in the isocyanate polyaddition process and, therefore, need not be removed or destroyed. On the contrary, these catalysts also accelerate the subsequent reactions.

The compounds according to the invention are valuable blocked reactants for the isocyanate polyaddition process and become active only in the presence of moisture and after hydrolytic splitting of the ring. Compounds according to the invention which still contain free isocyanate groups (n = 1 or 2) react under the influence of atmospheric moisture to give rise to high molecular weight polyaddition products without any further addition of isocyanate. However, these polyaddition products may also be reacted with further polyhydroxyl compounds to be converted by an NCO/OH addition reaction into higher functional potential reactants for polyisocyanates. Thus, for example, the reaction of 3 mols of a compound according to the invention in which m = 1 and n = 1 with 1 mol of a triol results in a derivative which contains three oxazolidine rings and which after hydrolytic splitting of the oxazolidine rings constitutes a reactant for polysiocyanates which is hexafunctional for the purpose of the isocyanate polyaddition reaction.

EXAMPLE 1

N-(2-Isopropyl-1,3-oxazolidin-3-yl)-ethoxycarbonyl benzylamine 133 g (1 mol) of benzylisocyanate is added dropwise to 159 g (1 mol) of 2-(2-isopropyl-1,3-oxazolidin-3-yl)-ethanol with vigorous stirring and the temperature is maintained at from 20° to 25° C with cooling. An almost colorless product with a viscosity of 460 cP (25° C) is obtained. It shows no NCO bands in the IR spectrum, but does show the expected urethane bands (1700 cm$^{-1}$, 1540 cm$^{-1}$).

EXAMPLE 2

N-(2-Isopropyl-1,3-oxazolidin-3-yl)-ethoxycarbonyl stearylamine 295 g of a mixture of hexadecylisocyanate and octadecylisocyanate (commercial stearylisocyanate, 14.8% NCO) are slowly added to 159 g (1 mol) of 2-(2-isopropyl-1,3-oxazolidin-3-yl)-ethanol and 0.1 g of Sn(II) octoate at room temperature with stirring. Stirring is continued for 5 hours at about 50° C after all the isocyanate has been added. The product solidifies after some time to a waxy mass which melts to a clear liquid at temperatures of from 65° to 70° C.

EXAMPLE 3

N,N'-Bis-[(2-isopropyl-1,3-oxazolidin-3-yl)-ethoxycarbonyl]-1,6-diaminohexane 159 g (1 mol) of 2-(2-isopropyl-1,3-oxazolidin-3-yl) ethanol are reacted with 84 g (0.5 mol) of hexamethylene diisocyanate in the presence of 0.1 g of Sn(II) octoate at 40° C by the method described in Example 1. Stirring is continued for 8 hours after all the isocyanate has been added. After 3 days, the product has a viscosity of about 15,000 cP (20° C).

EXAMPLE 4

N,N'-Bis-[(1,3-oxazolidin-3-yl)-ethoxycarbonyl]-1,6-diaminohexane 117 g (1 mol) of 2-(1,3-oxazolidin-3-yl)-ethanol are reacted with 84 g (0.5 mol) of hexamethylene diisocyanate in 20 g of xylene by the method described in Example 1. This reaction is catalyzed by the addition of 0.05 g of Sn(II) octoate and is carried out first at 30° C and later at 50° C. The product obtained, which is about 90% pure, is solid at room temperature, but a pourable liquid at 50° C.

EXAMPLE 5

N,N'-Bis-[(2-isopropyl-5-methyl-oxazolidin-3-yl)-propoxycarboxyl]-1,6-diaminohexane 187 g (1 mol) of 3-(2-isopropyl-5-methyl-1,3-oxazolidin-3-yl)-propanol-(2) are reacted with 84 g (0.5 mol) of hexamethylenediisocyanate, in the presence of 0.2 g of dibutyl-Sn(IV) dilaurate at from 40° to 50° C by the method described in Example 1 and the reaction mixture is then stirred for a further 6 hours.

The bisoxazolidine obtained is a colorless, viscous product which has a viscosity of 4420 cP at 50° C.

EXAMPLE 6

N,N'-Bis-[(2-isoproypl-oxazolidin-3-yl)-ethoxycarbonyl]-2,4-tolylenediamine 159 g (1 mol) of 2-(2-isopropyl-1,3-oxazolidin-3-yl)-ethanol are reacted with 87 g (0.5 mol) of tolylene-2,4-diisocyanate at temperatures of about 30° C by the method described in Example 1. The reaction is slightly exothermic. The product obtained is a yellowish, highly viscous liquid which is pourable at 60° C.

EXAMPLE 7

N-[(2-Isopropyl-1,3-oxazolidin-3-yl)-ethoxycarbonyl]-1-amino-6-isocyanato-hexane 159 g (1 mol) of 2-(2-isopropyl-1,3-oxazolidin-3-yl) ethanol are added slowly, with vigorous stirring, to 672 g (4 mol) of hexamethylenediisocyanate to which 0.02 g of Sn(II) octoate has previously been added. After 18 hours at room temperature, the reaction mixture is passed 2 to 4 times through a thin layer evaporator at from 160° to 170° C and 0.1 Torr. N-[(2-isopropyl-1,3-oxazolidin-3-yl)-ethoxy-carbonyl]-1-amino-6-isocyanato-hexane is obtained as a yellow product which contains at the most 0.4% of hexamethylene diisocyanate. (5500 cP, 25° C.).

EXAMPLE 8

N,N'-Bis-[(2-Isopropyl-5-methyl-1,3-oxazolidin-3-yl)-isopropoxycarbonyl]-1-aminomethyl-5-amino-1,3,3-trimethylcyclohexane 222 g (1 mol) of 1-isocyanatomethyl-5-isocyanato-1,3,3-trimethyl-cyclohexane are slowly added to 374 g (2 mol) of 3-(2-isopropyl-5-methyl-1,3-oxazolidin-3-yl)-propanol-(2) in the presence of 0.5 g of Sn(II) octoate by the method described in Example 1. The reaction mixture is heated to from 40° to 55° C for a further 20 hours after the slightly exothermic reaction has died down. In the final phase of the reaction, the reaction mixture is diluted with 31 g of xylene. A colorless 90% solution with a viscosity of 5360 at 50° C is thereby obtained.

EXAMPLE 9

222 g (1 mol) of 1-isocyanatomethyl-5-isocyanato-1,3,3-trimethyl-cyclohexane and 0.1 g of Sn(II) octoate are introduced into the reaction vessel and 159 g (1 mol) of 2-(2-isopropyl-1,3-oxazolidin-3-yl)-ethanol are slowly added with stirring. Stirring is then continued for a further 6 hours at 40° C. A mixture of oxazolidine urethane, oxazolidine urethane isocyanate and the diisocyanate used as starting material is thereby obtained. The reaction mixture is pourable at 40° C.

EXAMPLE 10

The procedure is the same as described in Example 9 but 168 g (1 mol) of hexamethylene diisocyanate and 159 g (1 mol) of 2-(2-isopropyl-1,3-oxazolidin-3-yl)-ethanol are used. A reaction mixture which contains NCO groups and oxazolidine rings and has a viscosity of 1000 cP (25° C) is obtained.

EXAMPLE 11

106 g (0.66 mol) of 2-(2-isopropyl-1,3-oxazolidin-3-yl) ethanol are added dropwise to 255 g (1 mol of NCO) of a 75% solution in ethyl glycol acetate/xylene (1:1) of a polyfunctional biuret polyisocyanate which has an NCO content of 16.5% (obtained according to German Patent No. 1,101,394 by biuretizing hexamethylene diisocyanate with water and then removing the free, unreacted hexamethylenediisocyanate) in the presence of 0.1 g of Sn(II) octoate. The reaction mixture is then stirred for a further 4 hours at from 35° to 40° C. A highly viscous reaction mixture which is pourable at 50° C is obtained after one day at room temperature.

EXAMPLE 12

The procedure is the same as indicated in Example 11, except that the quantity of 2-(2-isopropyl-1,3-oxazolidin-3-yl) ethanol is reduced to 53 g (0.33 mol). The product has a viscosity of 1250 cP at 25° C after 12 hours.

EXAMPLE 13

The procedure is the same as indicated in Example 11, but 159 g (1 mol) of 2-(2-isopropyl-1,3-oxazolidin-3-yl)-ethanol are used. The reaction product is solid at room temperature but may be poured at about 70° C.

EXAMPLE 14

79 g (0.5 mol) of 2-(2-isopropyl-1,3-oxazolidin-3-yl)-ethanol is added dropwise at room temperature to 600 g (0.2 mol) of an isocyanatoprepolymer which has an NCO content of 3.5%, by weight, and has been prepared by reacting 2,4-diisocyanatotoluene with a polyether which has been obtained by propoxylating an equimolar mixture of trimethylolpropane and 1,2-propanediol. The reaction mixture is then heated to 50° C for 6 hours. The end-product, which is free from NCO groups, has a viscosity of about 3600 cP (25° C).

EXAMPLE 15

The procedure is the same as indicated in Example 14, but the oxazolidine component used is 58 g (0.5 mol) of 2-(1,3-oxazolidin-3-yl)-ethanol. When all the reactants have been added together, the reaction mixture is diluted with 140 g of toluene and stirred for 10 hours. An almost colorless solution which has a viscosity of 17,800 cP (25° C) is obtained.

EXAMPLE 16

1500 g (0.5 mol) of the isocyanatoprepolymer from Example 14 are diluted with 72 g of xylene. 26.5 g (0.16 mol) of 2-(2-isopropyl-1,3-oxazolidin-3-yl)-ethanol are added dropwise at room temperature. The approximately 90% solution of high molecular weight oxazolidine isocyanate obtained has a viscosity of 3330 cP at 25° C.

EXAMPLE 17

1500 g (0.5 mol) of the isocyanatoprepolymer from Example 14 are diluted with 142 g of toluene, and 39.5 g (0.25 mol) of 2-(2-isopropyl-1,3-oxazolidin-3-yl)-ethanol are slowly added at room temperature. The approximately 80% solution of high molecular weight oxazolidine isocyanate has a viscosity of 1230 cP at 25° C.

EXAMPLE 18

80 g (0.5 mol) of 2-(2-isopropyl-1,3-oxazolidin-3-yl)-ethanol are slowly added at 20° C to 570 g (0.5 mol NCO) of an isocyanatoprepolymer which has been obtained by reacting 1 part, by weight, of 1-isocyanatomethyl-5-isocyanato-1,3,3-trimethyl-cyclohexane with 4 parts by weight of a linear polyether which in turn was obtained by propoxylating propylene glycol and has the OH number 56, and the reaction mixture is diluted after 2 hours with 70 g of toluene. The approximately 90% solution obtained has a viscosity of 690 cP at 25° C.

EXAMPLE 19

0.2 g of Sn(II) octoate is added to 570 g (0.5 mol NCO) of the prepolymer used in Example 18, and 58.5 g (0.5 mol) of 2-(1,3-oxazolidin-3-yl)-ethanol are then slowly added at room temperature. After 2 hours, the reaction mixture is diluted to a concentration of 80% with 157 g of toluene. The viscosity of the solution is 2200 cP at 25° C.

EXAMPLE 20

19.3 g (0.16 mol) of 2-(1,3-oxazolidin-3-yl)-ethanol are slowly added to 570 g (0.5 mol NCO) of the prepolymer used in Example 18 and the mixture is stirred for 3 hours. It is then diluted with 63 g of toluene. The solution of high molecular weight oxazolidine isocyanate has a viscosity of 4420 cP at 25° C.

EXAMPLE 21

70 g of tolylene-2,4-diisocyanate are added at 60° C to 400 g of a dihydroxypolyester which has been prepared by reacting adipic acid with excess quantities of ethylene glycol and which has an average molecular weight of 2,000. After completion of the reaction, the prepolymer prepared in this way has an NCO content of 4.5%. A mixture of 32 g (0.2 mol) of 2-(2-isopropyl-1,3-oxazolidin-3-yl)-ethanol and 85 g of xylene is added dropwise at 60° C. The high molecular weight oxazolidine isocyanate is solid at room temperature but becomes pourable at about 80° C.

EXAMPLE 22

0.1 g of Sn(II) octoate are added to 200 g of the linear hydroxypolyester used in Example 21 and 33.4 g (0.5 mol) of 1-isocyanatomethyl-5-isocyanato-1,3,3-trimethyl-cyclohexane are then slowly added at 60° to 70° C. After 18 hours at room temperature, a solution of 8 g (0.05 mol) of 2-(2-isopropyl-1,3-oxazolidin-3-yl)-ethanol in 60 g of xylene is added dropwise at from 90° to 100° C.

The 90% solution of the high molecular weight oxazolidine isocyanate becomes solid at room temperature but is pourable at about 70° C.

EXAMPLE 23

32.7 g (0.1 mol) of the oxazolidine isocyanate prepared in Example 7 are added dropwise at room temperature in the presence of 0.1 g of Sn(II) octoate to 148 g (1 mol of hydroxyl groups) of a branched polyether which has been prepared by propoxylating trimethylolpropane and which has a hydroxyl content of 12%, by weight.

After 2 days, the resulting oxazolidine polyhydroxyl compound has a viscosity of 2000 cP (25° C).

EXAMPLE 24

The procedure is as indicated in Example 23, only the quantity of oxazolidine isocyanate is increased to 163 g (0.5 mol). After 2 days, the polyfunctional oxazolidine hydroxyl compound obtained in this way has a viscosity of 27,500 cP (25° C).

EXAMPLE 25

0.05 g of Sn(II) octoate is added to 163 g (0.5 mol of hydroxyl groups) of 65% solution in ethylene glycol acetate/xylene (1:1) of a branched polyester which has a hydroxyl group content of 8%, by weight and which has been obtained by esterifying 1 mol of phthalic acid anhydride, 2 mols of hexahydrophthalic acid anhydride and 1 mol of maleic acid anhydride with 3.45 mol of trimethylolpropane. A solution in 44 g of ethylene glycol acetate/xylene (1:1) of 82 g (0.25 mol) of the oxazolidine isocyanate prepared in Example 7 is then added dropwise.

A viscous 65% solution of a polyester which contains hydroxyl groups and oxazolidine rings is obtained (viscosity at 50° C: 8700 cP).

EXAMPLE 26

The procedure is the same as described in Example 25, but using a solution in 600 g of ethylene glycol acetate/xylene (1:1) of 163 g (0.5 mol) of the oxazolidine isocyanate prepared in Example 7. After 2 days, the 30% solution of the polyoxazolidine urethane has a viscosity of 100 cP (25° C).

EXAMPLE 27

0.1 g of Sn(II) octoate is added to 200 g of the polyester from Example 21 at from 60° to 70° C and 33.3 g (0.15 mol) of 1-isocyanatomethyl-5-isocyanato-1,3,3-trimethyl-cyclohexane are added dropwise at this temperature and stirring is then continued for 4 hours at the same temperature. 8 g (0.05 mol) of 2-(2-isopropyl-1,3-oxazolidin-3-yl)-ethanol in 60 ml of xylene are then added and the reaction mixture is stirred for 2 hours.

The resulting oxazolidine isocyanate hardens to a synthetic resin (88° Shore A) in air at room temperature even when applied in layers 8 mm in thickness.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Compounds corresponding to the following general formula:

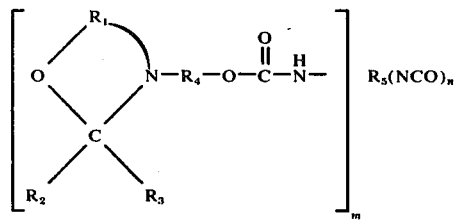

wherein
m represents an integer of from 1 to 6;
n represents an integer of from 0 and 4;
$R_1$ represents an aliphatic hydrocarbon group containing from 2 to 6 carbon atoms;
$R_2$ and $R_3$ which may be the same or different, each represents hydrogen, an aliphatic hydrocarbon containing from 1 to 4 carbon atoms, a cycloaliphatic hydrocarbon group containing from 5 to 7 carbon atoms, or an aromatic hydrocarbon group containing from 6 to 10 carbon atoms, or when taken together with the ring carbon atom they may form a 5- or 6-membered cycloaliphatic hydrocarbon ring;
$R_4$ represents an aliphatic hydrocarbon group containing from 2 to 6 carbon atoms; and
$R_5$ represents a residue of the type which may be obtained by removal of the isocyanate groups from an organic (n + m)-valent polyisocyanate.

2. Compounds of the formula given in claim 1 wherein m represents 1 or 2 and n represents an integer of from 0 to 2 and the sum of m + n equals 2 or 3; $R_1$ represents an aliphatic hydrocarbon group containing 2 or 3 carbon atoms, $R_2$ and $R_3$, which may be the same or different, each represents hydrogen or an aliphatic hydrocarbon group containing from 1 to 4 carbon atoms; $R_4$ represents an aliphatic hydrocarbon group cotaining 2 or 3 carbon atoms; and $R_5$ represents a residue of the type which may be obtained by removal of the isocyanate groups from an organic diisocyanate or triisocyanate.

3. Process for the preparation of urethanes which contain oxazolidine groups and optionally also isocyanate groups, characterized in that N-hydroxyalkyl-oxazolidines are reacted with organic polyisocyanates in an OH/NCO ratio of from 4:1 to 1:20.

4. Process according to claim 3, characterized in that N-hydroxyalkyl-oxazolidines are reacted with organic diisocyanates or triisocyanates in an OH/NCO ratio of 1:1 to 1:6.

5. A process for the preparation of oxazolidine containing urethanes comprising reacting N-hydroxyalkyl-oxazolidines of the formula

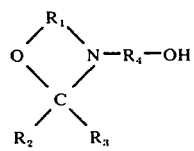

in which $R_1$-$R_4$ have the same meaning as in claim 1 with polyisocyanates of the formula

$R_5(NCO)_{m+n}$ in which n + m is 2 or 3 and $R_5$ is $C_4$ to $C_{12}$ alkyl, $C_5$-$C_{15}$ cycloalkyl, $C_6$-$C_{15}$ aryl, $C_7$-$C_{15}$ aralkyl, the residue of a di- or tri-isocyanate containing urea, allophanate, biuret, isocyanurate, carbodiimide or urethane groups or the residue after removing NCO groups of the reaction product of a diisocyanate with a di- or tri-hydroxy polyether having a molecular weight of about 400 to 10,000 said reaction being at an OH to NCO ratio of about 4:1 to 1:20 and a temperature of about 10° to 120° C.

6. In the process for preparing polyurethanes by reacting polyisocyanates with hydroxyl bearing compounds, the improvement comprising reacting the polyisocyanates with N-hydroxyalkyl oxazolidines of the formula

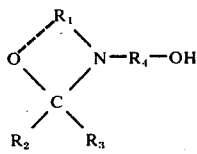

in which $R_1$ to $R_4$ have the same meaning as in claim 1.

* * * * *